United States Patent
Kuriloff et al.

[11] Patent Number: 5,318,565
[45] Date of Patent: Jun. 7, 1994

[54] SUCTION CAUTERY DISSECTOR

[75] Inventors: Daniel B. Kuriloff, 424 W. End Ave. Suite 11D, New York, N.Y. 10024; Robert K. Einhorn, 5109 Forbes Ave., Pittsburgh, Pa. 15213

[73] Assignees: Daniel B. Kuriloff, New York, N.Y.; Robert K. Einhorn; Ansel M. Schwartz, both of Pittsburgh, Pa.

[21] Appl. No.: 975,618

[22] Filed: Nov. 12, 1992

[51] Int. Cl.⁵ .................................. A61B 17/39
[52] U.S. Cl. ........................... 606/49; 604/119; 606/45; 606/42; 606/48
[58] Field of Search ............... 606/41, 42, 45, 46, 606/47, 48, 49; 604/119

[56] References Cited

U.S. PATENT DOCUMENTS

| | | | |
|---|---|---|---|
| 2,275,167 | 3/1942 | Bierman | 606/42 |
| 4,307,720 | 12/1981 | Weber, Jr. | 604/22 |
| 4,562,838 | 1/1986 | Walker | 606/42 |
| 4,724,836 | 2/1988 | Okada | 606/46 |
| 4,919,129 | 4/1990 | Weber, Jr. et al. | 606/42 |
| 5,030,218 | 7/1991 | Alexander | 606/49 |
| 5,098,430 | 3/1992 | Fleenor | 606/42 |

*Primary Examiner*—Ralph Lewis
*Assistant Examiner*—Sonya C. Harris
*Attorney, Agent, or Firm*—Ansel M. Schwartz

[57] ABSTRACT

The present invention pertains to a cautery dissector. The cautery dissector is comprised of a cautery blade and a handle member having a sheath portion and a device for adjustably retracting the cautery blade into the sheath portion. The cautery dissector also comprises a device for conducting electrical current to the tissues of the patient. Heat is generated within the tissue by communication between the cautery blade and the electrical dissecting unit. Preferably, the cautery dissector includes a suction system having a suction opening disposed adjacent to the cautery blade. Preferably, the cautery blade retracts into the sheath portion through a sheath opening which scrapes accumulated material from the cautery blade such that when the cautery blade is retracted into the sheath portion, the suction opening is unobstructed for suction. Preferably, a scraper member is disposed within the sheath member to assist in scraping accumulated material from the cautery blade. The present invention is also a method of cautery dissecting. The method includes the steps of performing surgery on a patient with a cautery dissector and retracting a blade of the cautery dissector through a scraping member of the cautery dissector to remove accumulated matter from the blade. Preferably, during the performing step, there is the step of maintaining suction through a suction opening of the cautery dissector which is disposed adjacent to the blade to remove smoke and debris.

9 Claims, 8 Drawing Sheets

SUCTION CAUTERY DISSECTOR

FIELD OF THE INVENTION

The present invention is related in general to medical devices. More specifically, the present invention is related to an improved cautery dissector.

BACKGROUND OF THE INVENTION

The use of a hand held cautery scalpel has become the preferred instrument for surgical dissection in many hospitals. Surgical elevation of flaps or dissection of tissue planes was in the past performed with either blunt dissection or with a traditional scalpel. A hand held suction cautery device or a hand held cautery scalpel with separate suction is often used interchangeably with a steel scalpel.

The cautery method hastens the operative procedure and reduces blood loss substantially. This is especially important for surgery on ill children or infants for whom even small blood losses are poorly tolerated. Limited bleeding is also advantageous when contamination from HIV infected blood is of concern.

The current design of commercially available suction cautery devices are not ideal for tissue dissection. With a typical hand held cautery device, the tubular design of the blade causes adherence of tissue to its tip causing excessive char and is difficult to clean. Further, the location of the momentary push button switch is awkward and not ergonomically placed to facilitate alternate control of suction and cauterization.

With scalpel cautery devices, suction of smoke is required, necessitating a second assistant for smoke evacuation.

The present invention combines the cutting blade of a hand held cautery scalpel and a suction channel disposed adjacent to the blade. The blade is retractable into a sheath that allows user control of the amount of exposure as well as automatic cleaning of char and tissue coagulum. The unique retractability of the blade allows rapid alternation between cutting and direct suctioning of blood and coagulation. The proximity of the suction tip to the blade permits instantaneous evacuation of the smoke plume generated by the cautery. Thus, the present invention refines the use of the cautery dissector and hastens the surgical procedure with reduction in blood loss.

SUMMARY OF THE INVENTION

The present invention pertains to a cautery dissector. The cautery dissector is comprised of a cautery blade and a handle member having a sheath portion and means for adjustably retracting the cautery blade into the sheath portion. The cautery dissector also comprises means for conducting electrical current to the tissues of the patient. The heating is generated within the tissue by communication between the cautery blade and the electrical dissecting unit.

Preferably, the cautery dissector includes a suction system having a suction opening disposed adjacent to the cautery blade. Preferably, the cautery blade retracts into the sheath portion through a sheath opening which scrapes accumulated material from the cautery blade such that when the cautery blade is retracted into the sheath portion, the suction opening is unobstructed for suction. Preferably, a scraper member is disposed within the sheath member to assist in scraping accumulated material from the cautery blade.

The cautery blade is retractable into the sheath portion to allow user control of the amount of exposure of the cautery blade as well as automatic cleaning of char and tissue coagulum from the cautery blade. The unique retractability of the cautery blade allows for rapid alternation between surgical cautery or cutting and direct suctioning of blood and coagulation. The proximity of the suction opening to the sheath opening permits essentially instantaneous evacuation of the smoke plum generated by the cautery blade. This hastens the surgical procedure resulting in a reduction of blood loss.

The present invention is also a method of cautery dissecting. The method includes the steps of performing surgery on a patient with a cautery dissector and retracting a blade of the cautery dissector through a scraping member of the cautery dissector to remove accumulated matter from the blade. Preferably, during the performing step, there is the step of maintaining suction through a suction opening of the cautery dissector which is disposed adjacent to the blade to remove smoke which would obscure visibility of the operative site and pose a health hazard to the surgeon. Preferably, after the retracting step, there is the step of collecting surgical debris through the suction opening of the cautery dissector with the blade in a retracted position.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1A:
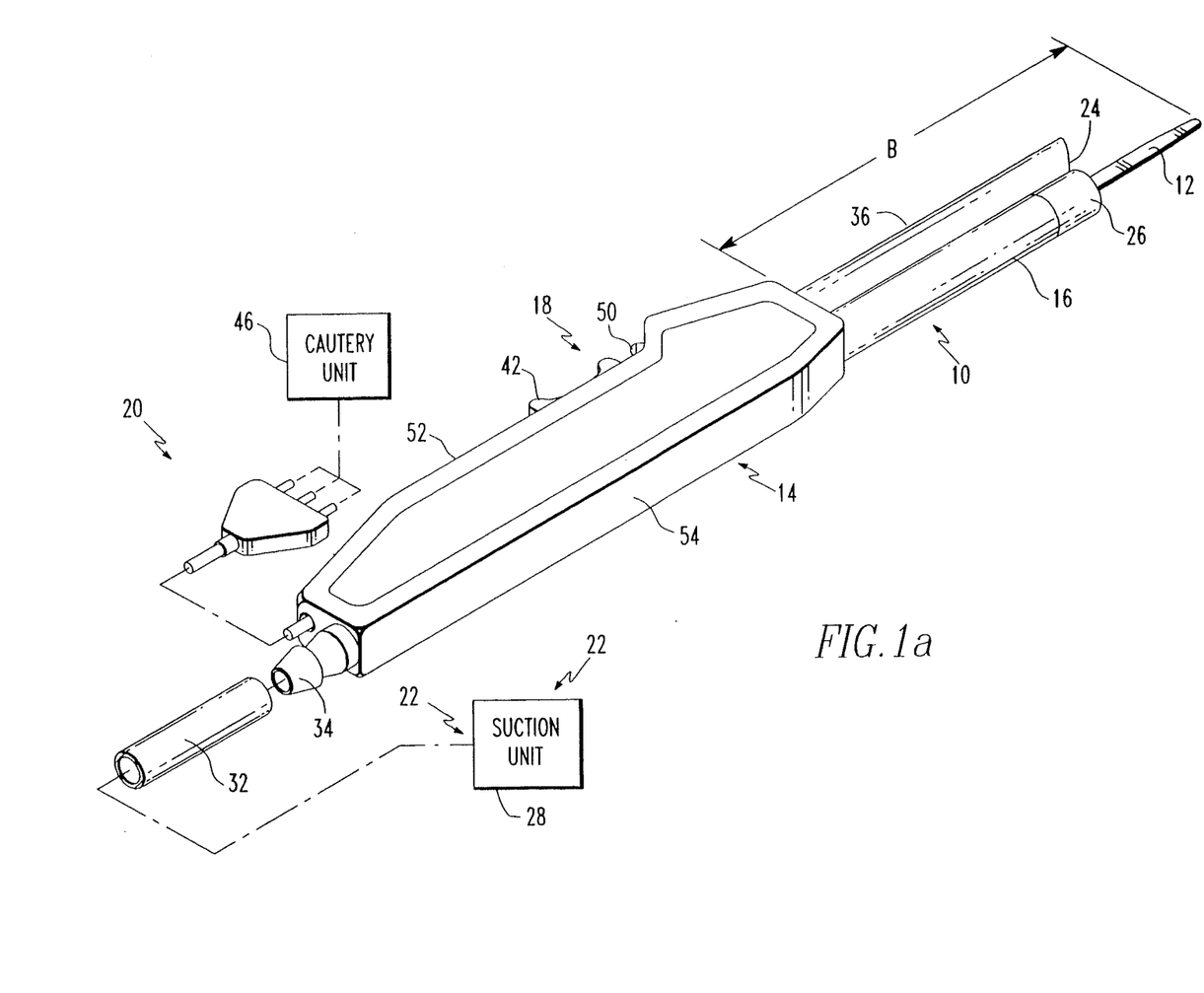
FIGS. 1a-1c are schematic representations showing the cautery dissector.
Figure 1B:
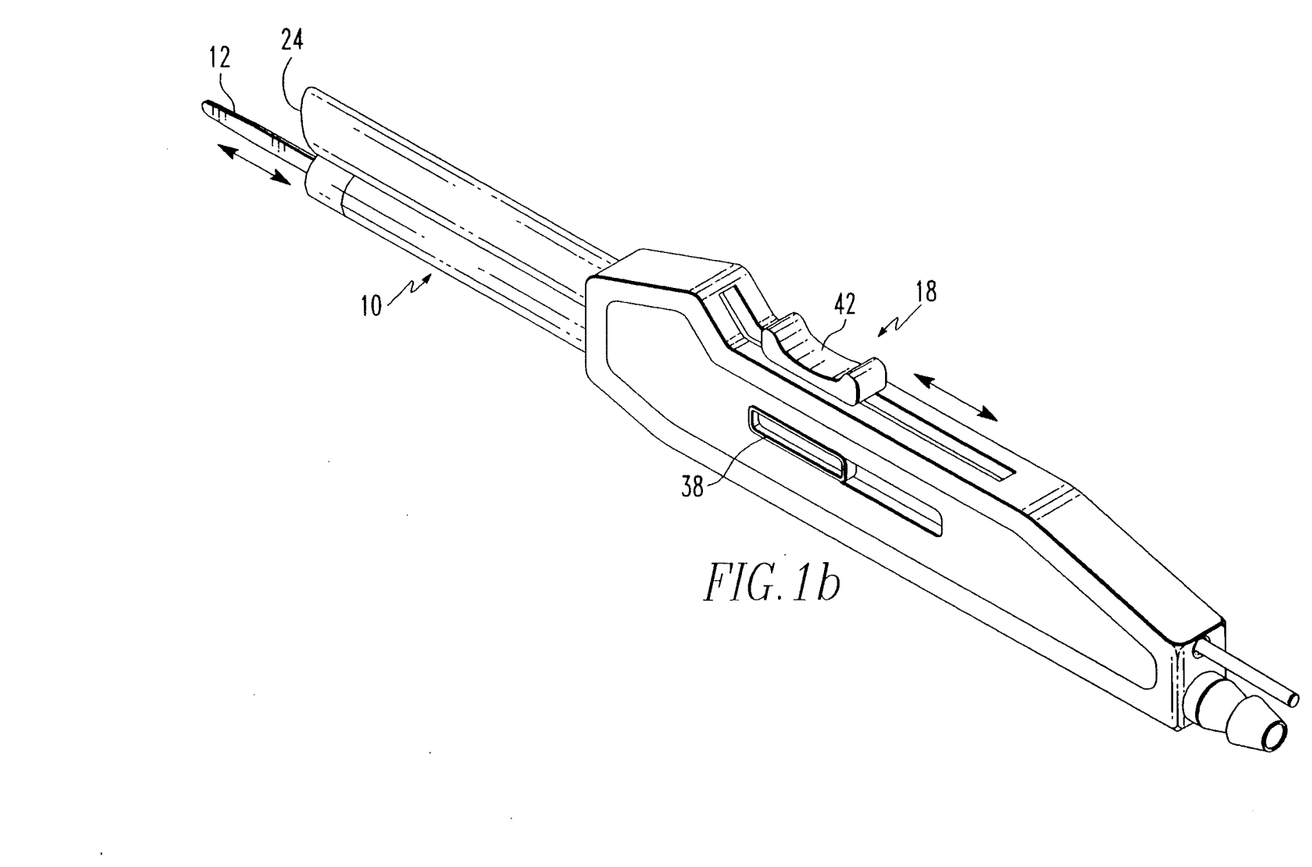
Figure 1C:
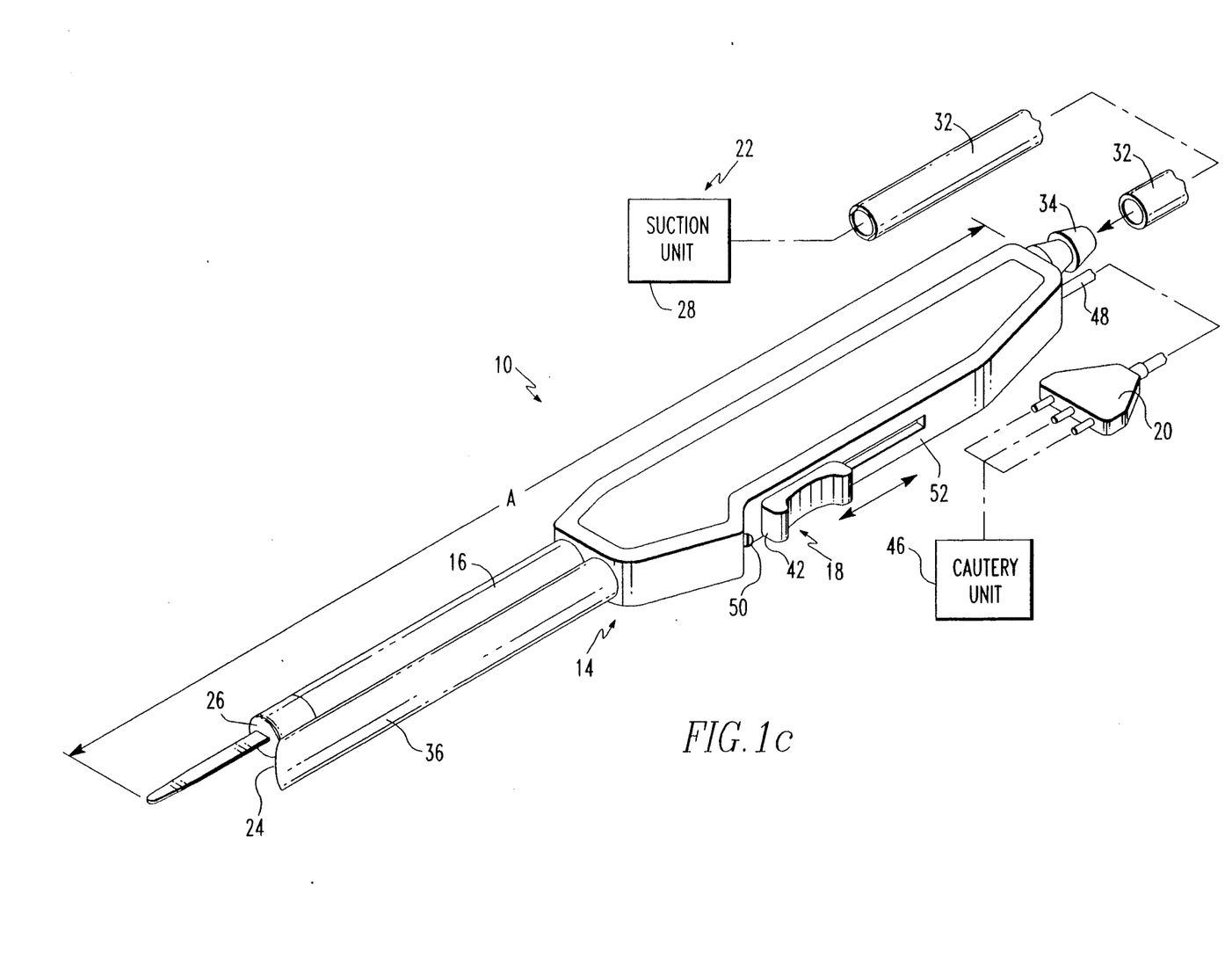

Referring now to the drawings wherein like reference numerals refer to similar or identical parts throughout the several views, and more specifically to FIGS. 1a-1c thereof, there is shown a cautery dissector 10. The cautery dissector 10 is comprised of a cautery blade 12 and a handle member 14 having a sheath portion 16 and means 18 for adjustably retracting the cautery blade 12 into the sheath portion 16. The cautery dissector 10 also comprises means 20 for conducting electrical current to the cautery blade 12. The heating means 20 is in electrical communication with the cautery blade 12. Preferably, the cautery blade 12 is coated with a non-stick coating, such as teflon, to prevent tissue coagulum and char from adhering to it. Preferably, the cautery blade 12 is flat and sharply pointed. Preferably, the cautery blade 12 is removable from the sheath portion 16 to allow it to be replaced. For instance, a needle tip can also be used for surgery.

Figure 2A:
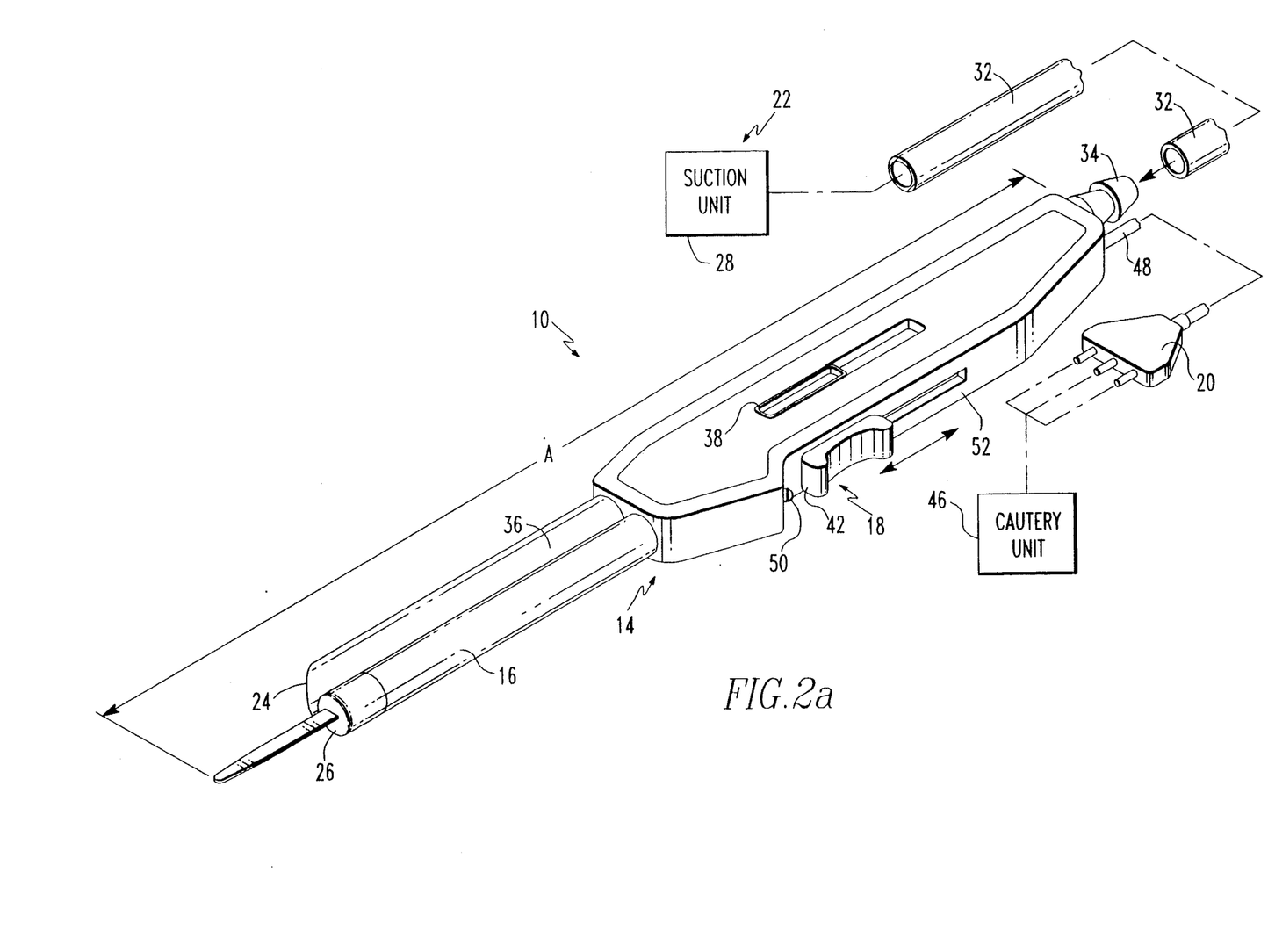
FIGS. 2a and 2b are schematic representations showing the cautery dissector.
Figure 2B:
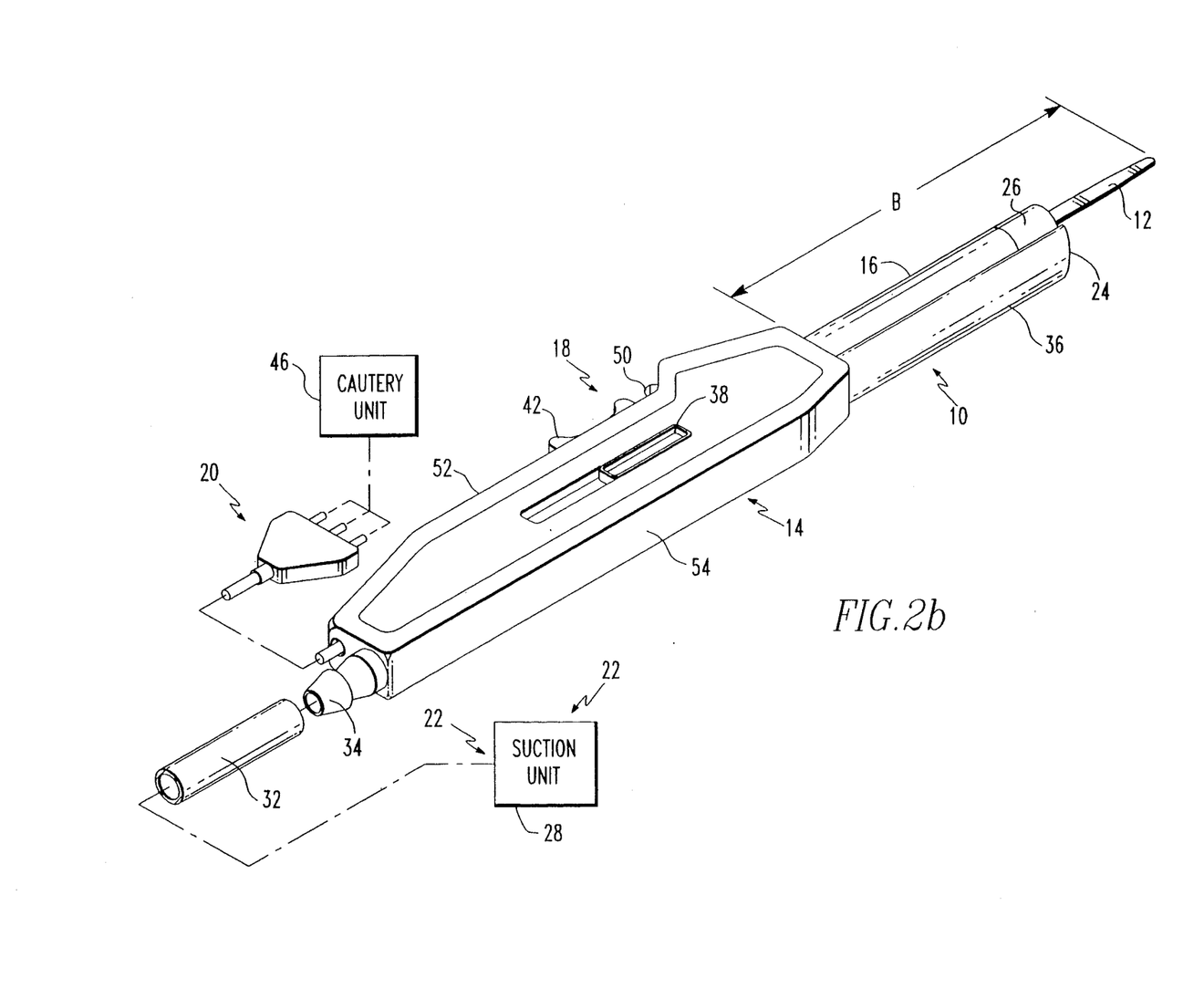

Preferably, as shown in FIGS. 2a and 2b, the cautery dissector 10 includes a suction system 22 having a suction opening 24 disposed adjacent to the cautery blade 12. Preferably, the cautery blade 12 retracts into the sheath portion 16 through a sheath opening 26 which scrapes accumulated material from the cautery blade 12 such that when the cautery blade 12 is retracted into the sheath portion 16, the suction opening 24 is unobstructed for suction.

The cautery blade 12 is retractable into the sheath portion 16 to allow user control of the amount of exposure of the cautery blade 12 as well as automatic cleaning of char and tissue coagulum from the cautery blade 12. The unique retractability of the cautery blade 12 allows for rapid alternation between surgical cautery, cutting, and direct suctioning of blood and coagulation. The proximity of the suction opening 24 to the sheath opening 26 permits essentially instantaneous evacuation of the smoke plum generated by the cautery blade 12. This improves visibility of the operative site, reduces toxic inhalation of smoke by the surgeon, reduces blood loss and hastens the overall surgical procedure.

Figure 3:
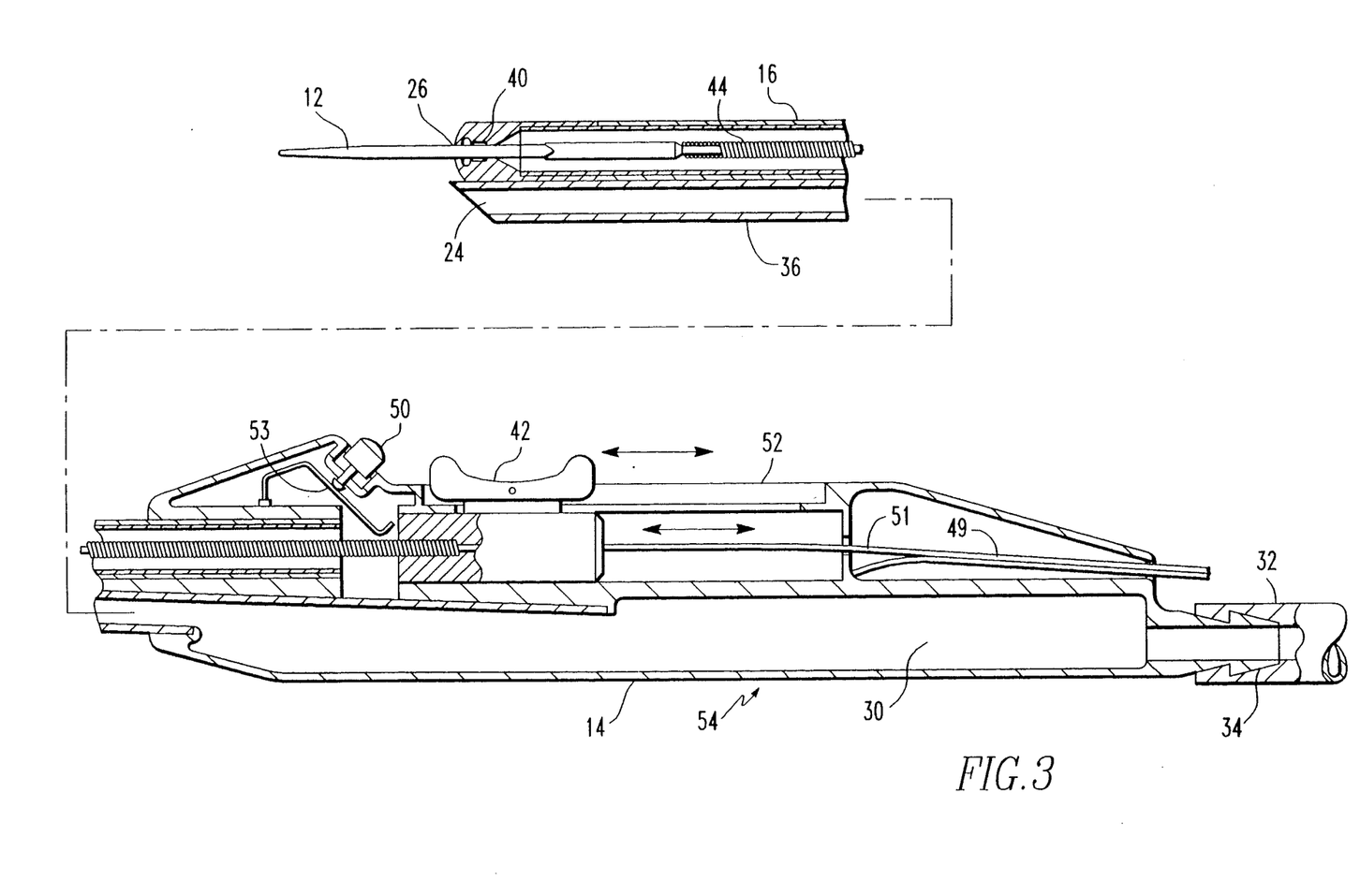
FIG. 3 is a schematic representation showing a cross section of the cautery dissector.

In a preferred embodiment, the suction system 22 includes a suction unit 28 for creating suction. As shown in FIG. 3 which is a cross section of the cautery dissector 10, a suction channel 30 is integrally disposed within the handle 14. Flexible tubing 32 fluidly connects the suction unit 28 to the suction channel 30, such as through a barbed nipple 34. A suction tube 36 extends from the suction channel 30 along the sheath portion 16 and terminates at the suction opening 24. Preferably, the suction channel 30 has a suction port 38 for controlling suction to the suction opening 24. When the suction port 38 is left uncovered, the suction unit draws suction primarily through the suction port 38 as opposed to the suction opening 24 at the end of the suction tube 36. In contrast, when the suction port 38 is covered, maximum suction is present at the suction opening 24.

Preferably, the suction tube 36 and the sheath portion 16 are malleable for allowing the suction tube 36 and the sheath portion 16 to be bent into a variety of positions to facilitate surgical dissection in tight places.

Preferably, as shown in FIG. 3, a scraper member 40 is disposed within the sheath portion 16 to assist in scraping accumulated material from the cautery blade 12. If, for instance, the sheath portion 16 is comprised of a medical grade plastic, the sheath opening 26 is toleranced to scrape most of the accumulated matter from the cautery blade 12. The sheath opening 26 being plastic cannot scrape all of the accumulated matter from the cautery blade since it is prone to wear and thus should not directly contact the cautery blade 12. The scraper member 40 is preferably comprised of a material, such as metal, having a greater wear resistance than plastic. The metal, in having a greater wear resistance, can be toleranced to directly scrape against the cautery blade 12 to remove any accumulated matter that the sheath opening 26 missed. In this manner, the cautery blade 12 can be easily cleaned by retracting it into the sheath portion 16. Further, while the cautery blade 12 is retracted, the suction opening 24 can collect the accumulated matter which was scraped off as well as any blood, debris and/or smoke resulting from the surgery. Preferably, the retracting means 18 includes a slide switch 42 disposed on the handle and a member 44 for connecting the cautery blade 14 to the slide switch 42.

Preferably, there is a cautery unit 46 for supplying power to the cautery blade 12, a wire 48 for providing electrical communication between the cautery unit 46 and the handle 14 and a power button 50 disposed on the handle for allowing selective electrical communication between the cautery unit 46 and the cautery blade 12. As shown in FIG. 3, the wire 48 from the cautery unit 46 enters the handle and comprises lead 49 and lead 51. Lead 49 is connected to the metal frame of the handle 14 while the lead 51 is connected to the slide switch 42 and member 40 in electrical communication with the cautery blade 12. Power button 50 forces spring member 53 down onto the member 44 to establish an electrical circuit between the frame of the handle and the cautery blade 12 to energize the cautery blade 12.

The slide switch 42, the power button 50 and the suction port should be ergonomically positioned on the handle 14, so that the surgeon's fingers can easily reach and operate them. Preferably, the slide switch 42 and the power button 50 are disposed on a first side 52 of the handle 14 with the power button 50 disposed above the slide switch 42. In this manner, the surgeon's thumb or index finger can operate both the power button 50 and the slide switch 42. The suction port 38 is preferably disposed on the second side 54 of the handle 14. In this manner, the surgeon, while grasping the handle 14, can cover and uncover the suction port 38 with his index finger or thumb, for example.

Figure 4:
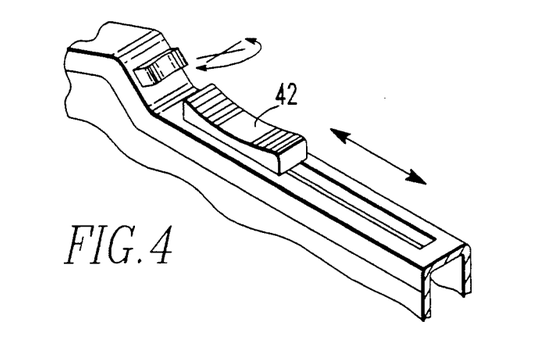
FIG. 4 is a schematic representation showing one embodiment of the power button.

In an alternative embodiment, and as shown in FIG. 4, the power button 50 can be designed as a rocker switch to control both coagulation and cutting modes of the cautery blade 12. For example, rocking the power button 50 right could activate the cutting mode, while rocking the power button 50 left could activate the coagulation mode.

Figure 5:
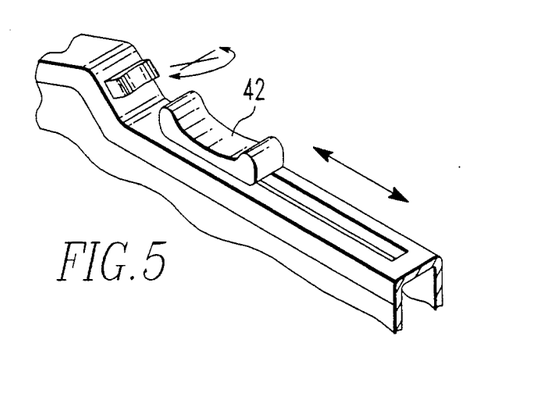
FIG. 5 is a schematic representation showing a triple-action slide switch.
Figure 6A:
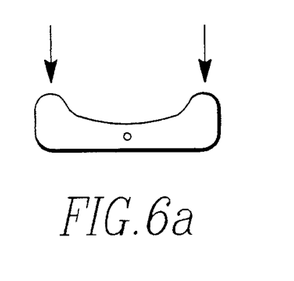
FIGS. 6a-6c are schematic representation showing the various modes of the triple-action slide switch.
Figure 6B:
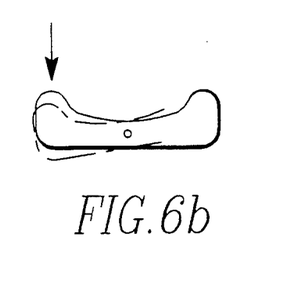
Figure 6C:
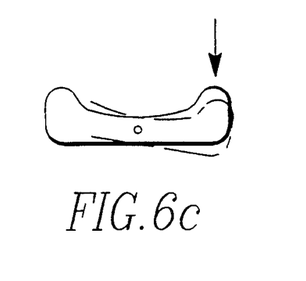

In another embodiment, and as shown in FIGS. 5 and 6, the slide switch 42 incorporates the function of the power button 50. For example, as shown in FIG. 6, the slide switch 42 can operate in three modes. In a first mode, as shown in FIG. 6a, with the slide switch 42 in a central position, the cautery blade 12 does not receive power. In a second mode, as shown in FIG. 6b, with the slide switch 42 pushed to the left, the cautery blade 12 operates in cutting mode. In a third mode, as shown in FIG. 6c, with the slide switch 42 pushed to the right, the cautery blade 12 operates in coagulation mode.

Figures 7A, 7B, 7C:
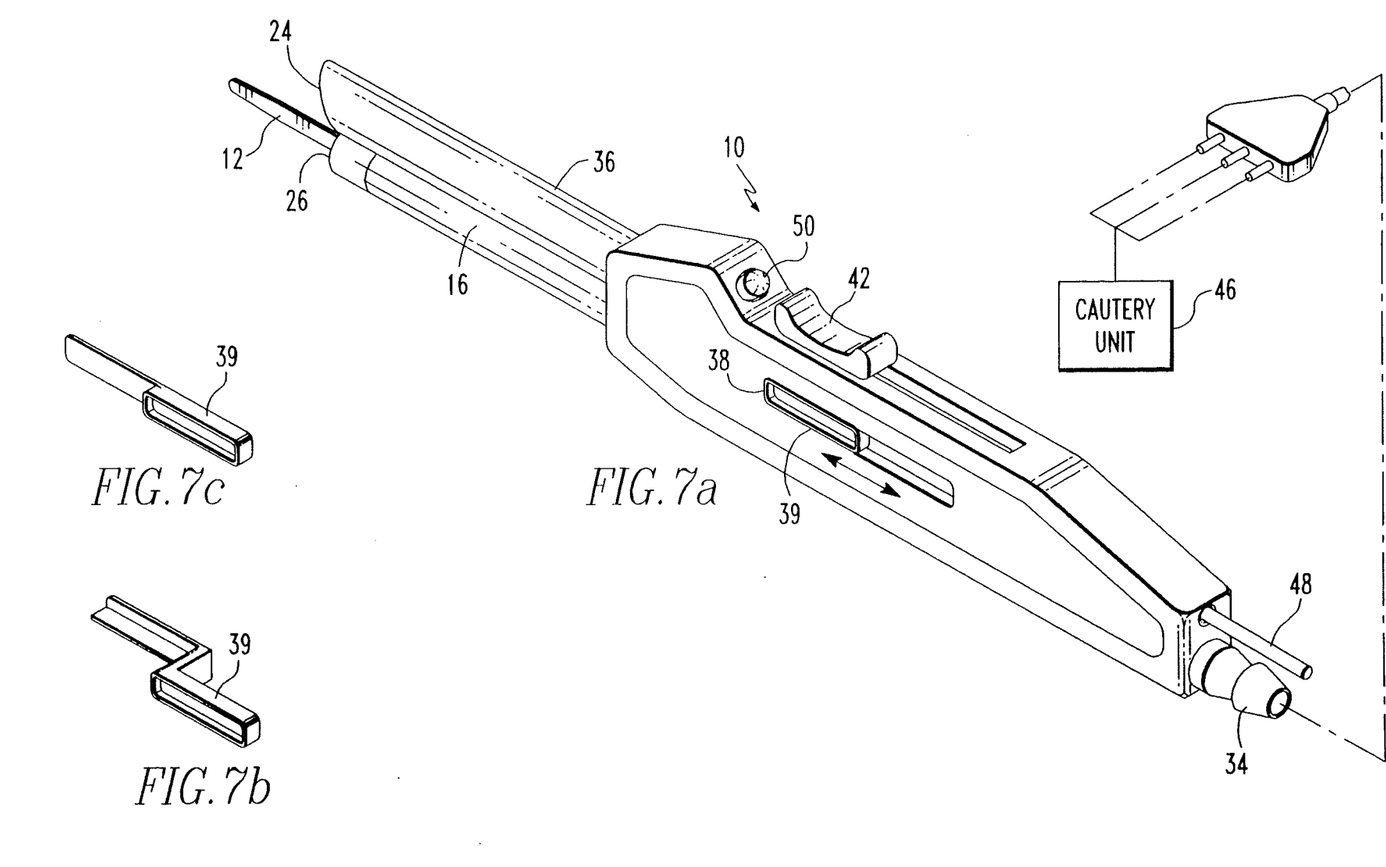
FIGS. 7a-7c are schematic representations showing the cautery dissector having an adjustable suction port and a blended current button.

In another embodiment and as illustrated in FIGS. 7a–7c, the suction port 38 is covered by a member 39 which adjustably covers the suction port 38 by sliding across it. In this manner, the suction through the suction opening 24 can be altered in degree by simply sliding the member 39 as desired amount over the suction port 38. FIG. 7b shows one embodiment of the sliding member. FIG. 7c shows another embodiment of the sliding member.

As shown in FIG. 7a, the cautery dissector 10 can also comprise a blended current switch 60. The cautery unit 46 or electrosurgical generator produces three types of radiofrequency waves: a sinusoidal wave form that has pure cutting properties; a dampened sine wave with pure coagulating properties; and a variable sine wave with a blended current that combines characteristics of the other two waves. The electrosurgical generator converts wall current (110 V, 60H) into high-frequency radiowaves in the range of 500,000 to 1,000,000H. This output is high-voltage, low-amperage current that electrodesiccates tissue. At the contact point, the electromagnetic waves result in a rapid to-and-fro motion of molecules; and because the tissue resists this motion, frictional heat is produced. The heating actually boils tissue fluid and results in desiccation. The dampened sine wave has excellent coagulating properties but results in marked tissue destruction and charring. The sinusoidal wave cuts through tissue with little thermal damage, much like a conventional scalpel, but has no hemostatic properties. Most surgical dissection is performed with a dampened sine wave output that cuts and coagulates simultaneously with minimal thermal destruction and charring. The blended current switch 60 causes the electrosurgical generator to produce a blended current. Pushing the slide switch 42 to the right would cause dampened sine wave current for coagulation while pushing the slide switch 42 to the left would cause continuous sine wave current for optimum cutting.

The present invention is also a method of cautery dissecting which comprises the steps of performing surgery on a patient with a cautery dissector 10 and retracting a blade 12 of the cautery dissector 10 through a scraping member of the cautery dissector 10 to remove accumulated matter from the blade 12. Preferably, during the performing step, there is the step of maintaining suction through a suction opening 24 of the cautery dissector 10 which is disposed adjacent to the blade 12. Preferably, after the retracting step, there is the step of collecting surgical debris through the suction opening 24 of the cautery dissector 10 with the blade 12 in a retracted position.

In the operation of the invention, the cautery dissector 10 is used, for instance, to remove the tonsils of a patient (not shown). The length of the cautery dissector 10, as represented by reference character A in FIG. 1c is 12 inches. The length of the sheath portion 16 and the extended cautery blade 12, as represented by reference character B in FIG. 1a, is 6 inches. The surgeon positions the cautery blade 12 adjacent to the tonsil to be removed and activates the cautery blade 12 by pressing the power button 50 with the thumb. The power button electrically connects the cautery unit 46 to the cautery blade 12 to cause heating of tissue in contact with the cautery blade 12 in a manner which is well known within the prior art. For example, the cautery blade 12 can be used to dissect tissue to remove the tonsil, while simultaneously coagulating any bleeding vessels. The proximity of the suction opening 24 to the cautery blade 12 permits instantaneous evacuation of the smoke plume generated by cauterization. The blood and coagulation resulting during cauterization is suctioned directly into the suction channel, by retracting the cautery blade 12 into the sheath portion 16 with the slide switch 42 to allow the suction opening 24 to be disposed directly against the surgical site. To control the amount of suction at the suction opening 24, the suction port 38 is selectively covered with the upper portion of the index finger or thumb. Maximum suction is present at the suction opening 24 when the suction port 38 is completely covered. While retracting, the cautery blade 12 is automatically cleaned of char and tissue coagulation by the sheath opening 26 and the scraper member 40.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A cautery dissector comprising:
   a cautery blade;
   a handle member having a sheath portion and means for adjustably retracting the cautery blade into the sheath portion, said retracting means connected to said cautery blade, said retracting means including a power rocker slide switch connected to the cautery blade;
   means for allowing electrical current to pass between the cautery blade and the patient's tissues for coagulation and/or cutting, said allowing means in electrical communication with the cautery blade, said allowing means connected to the power rocker slide switch such that the power rocker slide switch can operate in a first mode where the cautery blade does not receiver power, a second mode where the cautery blade operators in a cutting mode and a third mode where the cautery blade operates in coagulation mode; and
   a suction system having a suction opening disposed adjacent to cautery blade, said suction system comprising a suction port such that when the suction port is left uncovered, the suction system draws suction primarily through the suction port and when the suction port is completely covered, maximum suction is present at the suction openings, said suction port covered by a member slidably mounted within the handle member which adjustably covers the suction port by sliding across it so that suction through the suction opening can be altered in degree by sliding the member a desired amount over the suction port.

2. A cautery dissector as described in claim 1 wherein the cautery blade retracts into the sheath portion through a sheath opening, said sheath portion adapted for scraping accumulated material for said cautery blade.

3. A cautery dissector as described in claim 2 wherein the suction system includes a suction unit, a suction channel integrally disposed within said handle, flexible tubing connecting the suction unit to the suction channel and a suction tube extending adjacent to the sheath and terminating at the suction opening.

4. A cautery dissector as described in claim 3 wherein the suction tube and sheath portion are malleable for allowing the suction tube and the sheath portion to be bend in a variety of positions.

5. A cautery dissector as described in claim 4 wherein the sheath portion includes a scraper member for assisting in removing accumulated material on the cautery blade as the cautery blade is retracted into the sheath portion.

6. A cautery dissector as described in claim 5 wherein the allowing means includes a cautery unit for supplying power to the cautery blade, a wire for providing electrical communication between the cautery unit and the power button.

7. A cautery dissector as described in claim 6 wherein the handle has a first side and a second side, said power rocker slide switch disposed on said first side, sad suction port disposed on said second side.

8. A cautery dissector as described in claim 7 having a length of between 10–13 inches.

9. A cautery dissector as described in claim 8 wherein the cautery blade is coated with a non-stick material.

* * * * *